(12) United States Patent
Petzoldt et al.

(10) Patent No.: US 7,772,148 B2
(45) Date of Patent: Aug. 10, 2010

(54) HETEROGENEOUS CATALYST FOR THE PREPARATION OF ACROLEIN BY PARTIAL GAS PHASE OXIDATION OF PROPENE

(75) Inventors: Jochen Petzoldt, Weisenheim am Berg (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 570 days.

(21) Appl. No.: 11/627,573

(22) Filed: Jan. 26, 2007

(65) Prior Publication Data

US 2007/0142223 A1   Jun. 21, 2007

Related U.S. Application Data

(62) Division of application No. 10/974,831, filed on Oct. 28, 2004, now Pat. No. 7,208,636.

(60) Provisional application No. 60/520,660, filed on Nov. 18, 2003.

(30) Foreign Application Priority Data

Nov. 18, 2003   (DE) ................................ 103 53 954

(51) Int. Cl.
*B01J 27/192* (2006.01)
*B01J 21/00* (2006.01)
*B01J 23/00* (2006.01)

(52) U.S. Cl. ........................ 502/255; 502/212; 502/240; 502/321

(58) Field of Classification Search ................. 502/311, 502/212, 240, 248, 255, 321
See application file for complete search history.

(56) References Cited

U.S. PATENT DOCUMENTS

| 5,364,825 | A | * | 11/1994 | Neumann et al. ........... 502/311 |
| 5,449,821 | A | | 9/1995 | Neumann et al. |
| 6,166,263 | A | | 12/2000 | Etzkorn et al. |
| 6,383,976 | B1 | | 5/2002 | Arnold et al. |
| 6,525,217 | B1 | | 2/2003 | Unverricht et al. |
| 6,881,702 | B2 | * | 4/2005 | Arnold et al. ............... 502/311 |
| 2004/0034249 | A1 | | 2/2004 | Arnold et al. |
| 2004/0191953 | A1 | | 9/2004 | Dieterle et al. |

FOREIGN PATENT DOCUMENTS

| DE | 198 55 913 A1 | 6/2000 |
| DE | 199 48 248 A1 | 4/2001 |
| DE | 199 48 523 A1 | 4/2001 |
| DE | 103 13 209 A1 | 3/2004 |
| DE | 103 44 149 A1 | 4/2004 |
| DE | 103 50 812 | 6/2005 |

(Continued)

*Primary Examiner*—Taylor Victor Oh
(74) *Attorney, Agent, or Firm*—Oblon, Spivak, McClelland, Maier & Neustadt, L.L.P.

(57) ABSTRACT

An annular unsupported catalyst for the heterogeneously catalyzed partial gas phase oxidation of propene to acrolein at a propene hourly space velocity on the fixed catalyst bed of $\geq 120$ l (STP)/l·h and a total $CO_2$ and saturated hydrocarbon content of the starting reaction gas mixture of below 15 mol %, the catalysts of the fixed catalyst bed are the annular unsupported catalysts whose active composition is a multimetal oxide in which the molar Co/Fe ratio=from 2 to 4 and the molar Co/Mo ratio=from 0.3 to 0.7.

14 Claims, 1 Drawing Sheet

FOREIGN PATENT DOCUMENTS

| | | |
|---|---|---|
| DE | 103 51 269 | 6/2005 |
| EP | 0 293 224 A1 | 11/1988 |
| EP | 0 575 897 | 12/1993 |
| JP | 2002539100 | 11/2002 |
| WO | WO 02/24620 A2 | 3/2002 |

\* cited by examiner

HETEROGENEOUS CATALYST FOR THE PREPARATION OF ACROLEIN BY PARTIAL GAS PHASE OXIDATION OF PROPENE

CROSS REFERENCE TO RELATED APPLICATIONS

This application is a divisional application of prior U.S. patent application Ser. No. 10/974,831, filed Oct. 28, 2004.

BACKGROUND OF THE INVENTION

1. Field of the Invention

The present invention relates to a process for preparing acrolein by heterogeneously catalyzed partial gas phase oxidation, by conducting a starting reaction gas mixture which comprises propene, molecular oxygen and at least one inert gas and contains the molecular oxygen and the propene in a molar $O_2:C_3H_6$ ratio of $\geq 1$, and also carbon dioxide and saturated hydrocarbons together in a total amount of at most 15 mol %, at elevated temperature and at an hourly space velocity on the fixed catalyst bed of propene contained in the starting reaction gas mixture of $\geq 120$ l (STP)/l·h through a fixed catalyst bed whose catalysts are annular unsupported catalysts whose active composition is at least one multimetal oxide of the general formula I,

$$Mo_{12}W_aCO_bFe_cBi_dSi_eK_fO_n \quad (I)$$

where
- a=from $\geq 1$ to $\leq 3$,
- b=from $\geq 3$ to $\leq 8$,
- c=from $\geq 1$ to $\leq 4$,
- d=from $\geq 0.5$ to $\leq 1.5$,
- e=from $\geq 0$ to $\leq 10$,
- f=from $\geq 0$ to $\leq 0.2$ and
- n=a number which is determined by the valency and frequency of the elements in I other than oxygen, in such a way that the propene conversion in a single pass is $\geq 90$ mol % and the associated selectivity of acrolein formation is $\geq 80$ mol %.

2. Description of the Background

Acrolein is a reactive monomer which is especially significant as an intermediate, for example in the preparation of acrylic acid by two-stage heterogeneously catalyzed partial gas phase oxidation of propene. Acrylic acid is suitable as such or in the form of its alkyl esters, for example, for preparing polymers which may find use, inter alia, as adhesives or water-absorbent materials.

The preparation of acrolein by the heterogeneously catalyzed partial gas phase oxidation process as described in the preamble of this document is known (cf., for example, DE-A 10351269, DE-A 10350812, DE-A 10344149, DE-A 19948523, DE-A 10313209, DE-A 19948248, DE-A 19855913 and WO 02/24620). Typically, it forms the first stage of a two-stage heterogeneously catalyzed gas phase partial oxidation of propene to acrylic acid. In the first reaction stage, the propene is substantially partially oxidized to acrolein and, in the second reaction stage, the acrolein formed in the first reaction stage is substantially partially oxidized to acrylic acid. It is significant that the industrial embodiment is normally configured in such a way that the acrolein formed in the first reaction stage is not removed, but rather conducted into the second reaction stage as a constituent of the product gas mixture leaving the first reaction stage, optionally supplemented by molecular oxygen and inert gas, and optionally cooled by direct and/or indirect cooling.

The target product of a heterogeneously catalyzed partial gas phase oxidation of propene to acrolein is acrolein.

A problem in all heterogeneously catalyzed gas phase partial oxidations in a fixed catalyst bed is that the reaction gas mixture, as it flows through the fixed catalyst bed, passes through a maximum value (known as the hotspot value).

This maximum value is composed of the external heating of the fixed catalyst bed and the heat of reaction. For reasons of suitability, the temperature of the fixed catalyst bed and the effective temperature of the fixed catalyst bed are therefore also distinguished from each other. In this context, the temperature of the fixed catalyst bed refers to the temperature of the fixed catalyst bed when the partial oxidation process is performed, but in the theoretical absence of a chemical reaction (i.e. without the influence of the heat of reaction). In contrast, effective temperature of the fixed catalyst bed refers to the actual temperature of the fixed catalyst bed taking into account the heat of reaction of the partial oxidation. When the temperature of the fixed catalyst bed is not constant along the fixed catalyst bed (for example in the case of a plurality of temperature zones), the term temperature of the fixed catalyst bed means the (numerical) average of the temperature along the fixed catalyst bed. It is significant in the aforementioned context that the effective temperature of the fixed catalyst bed likewise passes through the hotspot value with the temperature of the reaction gas mixture in the flow direction of the reaction gas mixture.

Disadvantages of the known processes according to the preamble of this document are that, for a given conversion of propene (based on single pass of the reaction gas mixture), the hotspot temperatures of the fixed catalyst bed associated with the catalysts recommended in the prior art, at the required propene hourly space velocities on the fixed catalyst bed, are too high (high hotspot temperatures are normally disadvantageous in that high temperatures firstly accelerate the aging process of the fixed catalyst bed (certain movement processes within the active composition of the catalysts which contribute to aging proceed, for example, more rapidly) and secondly reduce the selectivity of target product formation), which is why the catalysts in the prior art are generally present in the fixed catalyst bed necessarily diluted with inert material according to specific dilution profiles. However, for a given conversion of propene, the latter limits the possible hourly space velocity on the fixed catalyst bed of propene present in the starting reaction gas mixture.

SUMMARY OF THE INVENTION

It is an object of the present invention to provide a process as described at the outset of this document, except that the catalysts are selected in such a way that, especially at high propene hourly space velocity on the fixed catalyst bed, the given propene conversion is achieved at reduced hotspot temperature of the fixed catalyst bed and increased target product selectivity is achieved.

We have found that this object is achieved by a process for preparing acrolein by heterogeneously catalyzed partial gas phase oxidation, by conducting a starting reaction gas mixture which comprises propene, molecular oxygen and at least one inert gas and contains the molecular oxygen and the propene in a molar $O_2:C_3H_6$ ratio of $\geq 1$, and also carbon dioxide and saturated hydrocarbons together in a total amount of at most 15 mol %, at elevated temperature and at an hourly space velocity on the fixed catalyst bed of propene contained in the starting reaction gas mixture of $\geq 120$ l (STP)/l·h through a fixed catalyst bed whose catalysts are annular unsupported catalysts whose active composition is at least one multimetal oxide of formula I,

$$Mo_{12}W_aCo_bFe_cBi_dSi_eK_fO_n \qquad (I)$$

where
a=from $\geq 1$ to $\leq 3$,
b=from $\geq 3$ to $\leq 8$,
c=from $\geq 1$ to $\leq 4$,
d=from $\geq 0.5$ to $\leq 1.5$,
e=from $\geq 0$ to $\leq 10$,
f=from $\geq 0$ to $\leq 0.2$ and
n=a number which is determined by the valency and frequency of the elements in I other than oxygen, in such a way that the propene conversion in a single pass is $\geq 90$ mol % and the associated selectivity of acrolein formation is $\geq 80$ mol %, wherein, in the multimetal oxide composition I, the following molar ratios are additionally fulfilled: Co/Fe=from 2 to 4 and Co/Mo=from 0.3 to 0.7 or to 0.6.

BRIEF DESCRIPTION OF THE DRAWINGS

The FIGURE shows the pore distribution of a comparative annular unsupported catalyst CS of the invention.

DETAILED DESCRIPTION OF THE PREFERRED EMBODIMENTS

Figure 1:
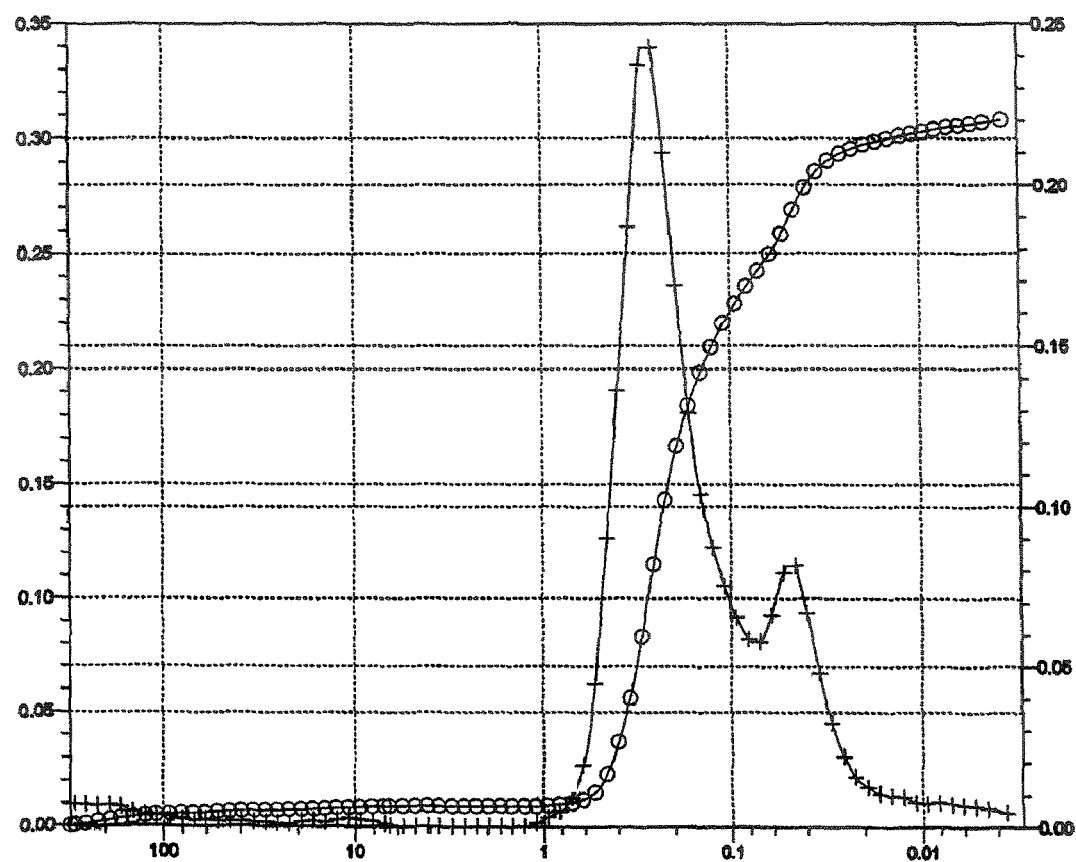

Multimetal oxide I catalysts for which the aforementioned ratios are fulfilled have already been used in EP-A 293224 for the heterogeneously catalyzed partial oxidation of propene to acrolein under high propene hourly space velocity on the fixed catalyst bed. However, this was under the prerequisite that the content of the starting reaction gas mixture of carbon dioxide and saturated hydrocarbons together was $\geq 20\%$ by volume (it will be appreciated that the process according to the invention can also be performed under these conditions in a noninventive manner).

DE-A 19948523 discloses that the annular catalyst geometry for heterogeneously catalyzed partial oxidations with high reactant hourly space velocity on the fixed catalyst bed is particularly advantageous.

According to the invention, the stoichiometric coefficient a is preferably from 1.5 to 2.5 and is more preferably from 2 to 2.5.

According to the invention, the stoichiometric coefficient b is preferably $\geq 4$ and $\leq 8$, more preferably $\geq 5$ and $\leq 8$ and most preferably $\geq 6$ and $\leq 8$ or $\geq 6.5$ and $\leq 7.5$.

According to the invention, the stoichiometric coefficient c is advantageously from $\geq 2$ to $\leq 4$ and more advantageously from $\geq 2.5$ to $\leq 3.5$.

In addition, it is favorable for the process according to the invention when the stoichiometric coefficient d is from 1 to 1.5.

It is also advantageous for the process according to the invention when the stoichiometric coefficient c is from $\geq 0.5$ to $\leq 3$, and particularly advantageous when c is $\geq 1$ or $\geq 1.5$ and $\leq 2.5$ or $\leq 2$.

The stoichiometric coefficient f is preferably in the range from $\geq 0.01$ to $\leq 0.15$ and most preferably in the range from $\geq 0.05$ to $\leq 0.1$.

At first, the aforementioned preferred ranges each apply independently. However, it is particularly advantageous when a plurality of them (and very particularly advantageously when all of them) are simultaneously fulfilled.

Independently of the aforementioned preferred ranges, it is advantageous for the process according to the invention when the molar Co/Fe ratio is from 2 to 3.5, or better from 2 to 3, or even better from 2 to 2.5.

It is also favorable for the process according to the invention, independently of the preferred ranges already mentioned, when the molar Co/Mo ratio is from 0.4 to 0.7 or to 0.6, better from 0.45 to 0.7 or to 0.6, even better from 0.5 to 0.7 or to 0.6 and at best from 0.55 to 0.7 or to 0.6.

Particularly advantageously, independently of the other preferred ranges for the stoichiometric coefficients a to f, the two aforementioned molar Co/Fe and Co/o ratios are simultaneously within the aforementioned preferred ranges. At best, both the stoichiometric coefficients a to f and the molar Co/Fe and Co/Mo ratios are within their preferred ranges.

It is essential to the invention that the catalysts of the fixed catalyst bed are annular unsupported catalysts. In other words, the active composition is not applied to an inert support body, but rather the entire annular shaped catalyst body consists of catalytically active multimetal oxide I.

Advantageously in accordance with the invention, their annular geometry (as always in this document, without taking into account any existing curvature of the top surface) has a length L of from 2 to 11 mm, an external diameter E of from 2 to 11 mm and a wall thickness W of from 0.5 to 5 mm.

In the case of unsupported catalyst rings which are suitable in accordance with the invention, useful unsupported catalyst rings are also especially those for which the internal diameter I is from 0.1 to 0.7 times the external diameter and the length is from 0.5 to 2 times the external diameter.

Unsupported catalyst rings whose use is favorable in accordance with the invention are also those having an external diameter of from 2 to 10 mm (or from 3 to 7 mm), an internal ring diameter of at least 1 mm, a wall thickness of from 0.5 to 2 mm (or from 0.75 mm to 1.75 mm) and a length (height) of from 2 to 10 mm (or from 2 to 5 mm).

Frequently, for unsupported catalysts which are very particularly suitable in accordance with the invention, the external diameter will be from 5.5 to 7 mm, the height (length) from 2.8 to 3.2 mm and the internal diameter from 3.5 to 5 mm. Typical wall thicknesses are from 1.0 to 1.7 mm, preferably from 1.3 to 1.7 mm and most preferably 1.5 mm.

In other words, hollow cylinder unsupported catalyst geometries which are suitable in accordance with the invention are, for example, (in each case external diameter×height× internal diameter, and, as always in this document, without taking into account any existing curvature of the top surface) are the geometries 6 mm×3 mm×4 mm, 5 mm×3 mm×2 mm, 6.5 mm×3 mm×4.5 mm, 5 mm×2 mm×2 mm, 5 mm×3 mm×3 mm, 6 mm×3 mm×3 mm, 7 mm×3 mm×4 mm, 7 mm×3 mm×5 mm and 5.5 mm×3 mm×3.5 mm.

The top surfaces of the catalyst ring geometries which are suitable in accordance with the invention may either both be, or only one may be, curved as described in EP-A 184790, and, for example, in such a way that the radius of the curvature is preferably from 0.4 to 5 times the external diameter. Preference is given in accordance with the invention to both top surfaces being uncurved.

The annular unsupported catalysts to be used in accordance with the invention may be prepared in a simple manner by generating from sources of the elemental constituents of the active composition a finely divided shapeable mixture and shaping from this mixture, optionally after adding shaping and/or reinforcing assistants, annular shaped unsupported catalyst precursor bodies, whose top surfaces are curved and/or uncurved, and converting them to the desired unsupported catalysts by thermally treating at elevated temperature.

Advantageously in accordance with the invention, the side crushing strength of the annular shaped unsupported catalyst precursor bodies is $\geq 10$ N and $\leq 25$ N, more advantageously $\geq 12$ N and 23 N or $\geq 13$ N and $\leq 22$ N, and very particularly advantageously $\geq 14$ N and $\leq 21$ N or $\geq 15$ N and $\leq 20$ N.

According to the invention, the particle size of the finely divided shapeable mixture to be shaped to annular shaped unsupported catalyst precursor bodies is also advantageously from 200 μm to 1.5 mm, more advantageously from 400 μm to 1 mm. In a favorable manner, at least 95 or 98 or more % by weight of the overall composition is within this particle size range.

In this document, side crushing strength refers to the crushing strength when the annular shaped unsupported catalyst precursor body is compressed at right angles to the cylindrical shell (i.e. parallel to the surface of the ring orifice).

All side crushing strengths in this document relate to a determination by means of a material testing machine from Zwick GmbH & Co. (D-89079 Ulm) of the Z 2.5/TS1S type. This material testing machine is designed for quasistatic stress having a single-impetus, stationary, dynamic or varying profile. It is suitable for tensile, compressive and bending tests. The installed force transducer of the KAF-TC type from A.S.T. (D-01307 Dresden) having the manufacturer number 03-2038 was calibrated in accordance with DIN EN ISO 7500-1 and could be used for the 1-500 N measurement range (relative measurement uncertainty: ±0.2%).

The measurements were carried out with the following parameters:

Initial force: 0.5 N.

Rate of initial force: 10 mm/min.

Testing rate: 1.6 mm/min.

The upper die was initially lowered slowly down to just above the surface of the cylindrical shell of the annular shaped unsupported catalyst precursor body. The upper die was then stopped, in order subsequently to be lowered at the distinctly slower testing rate with the minimum initial force required for further lowering.

The initial force at which the annular shaped unsupported catalyst precursor body exhibits crack formation is the side crushing strength (SCS).

Useful shaping assistants (lubricants) for preparing the annular shaped unsupported catalyst precursor bodies are, for example, carbon black, stearic acid, starch, polyacrylic acid, mineral or vegetable oil, water, boron trifluoride or graphite. Glycerol and cellulose ether may also be used as lubricants. Based on the composition to be shaped to the shaped unsupported catalyst precursor body, generally $\leq 5\%$ by weight, usually $\leq 3\%$ by weight, in many cases $\leq 2\%$ by weight, of shaping assistant is used. Typically, the aforementioned addition amount is $\geq 0.5\%$ by weight. The preferred lubricating assistant in accordance with the invention is graphite.

In the course of the thermal treatment of the annular shaped unsupported catalyst precursor bodies, the shaping assistants are usually substantially decomposed to gaseous components and/or combusted, so that the resulting annular unsupported catalyst is normally partly or completely free of shaping assistants used. When shaping assistant is present in the annular unsupported catalysts obtainable in accordance with the invention, it behaves substantially inertly with respect to the partial oxidation of propene to acrolein which is catalyzed by the unsupported catalysts.

The latter is also true of any finely divided reinforcing agents added before the shaping, such as microfibers of glass, asbestos, silicon carbide or potassium titanate. The shaping to the annular shaped unsupported catalyst precursor body may be carried out, for example, by means of a tableting machine, an extrusion shaping machine, an extrudate press or the like.

The annular shaped unsupported catalyst precursor body is thermally treated generally at temperatures which exceed 350° C. However, the temperature in the course of the thermal treatment will not normally exceed 650° C. Advantageously in accordance with the invention, the temperature in the course of the thermal treatment will not exceed 600° C., preferably 550° C. and more preferably 500° C. In addition, the temperature in the course of the thermal treatment of the annular shaped unsupported catalyst precursor body in the process according to the invention will preferably exceed 380° C., advantageously 400° C., particularly advantageously 420° C. and most preferably 440° C. The thermal treatment may also be subdivided into a plurality of sections within its duration. For example, a thermal treatment may initially be carried out at a temperature of from 150 to 350° C., preferably from 220 to 280° C., and be followed by a thermal treatment at a temperature of from 400 to 600° C., preferably from 430 to 550° C.

Normally, the thermal treatment of the annular shaped unsupported catalyst precursor body takes several hours (usually more than 5 h). Frequently, the overall duration of the thermal treatment extends for more than 10 h. Usually, treatment durations of 45 h or 25 h are not exceeded in the course of the thermal treatment of the annular shaped unsupported catalyst precursor body. Often, the overall treatment time is below 20 h. Advantageously in accordance with the invention, 500° C. (460° C.) are not exceeded in the course of the thermal treatment of the annular shaped unsupported catalyst precursor body, and the treatment time within the temperature window of $\geq 400°$ C. ($\geq 440°$ C.) extends to from 5 to 20 h.

The thermal treatment (and also the decomposition phase addressed hereinbelow) of the annular shaped unsupported catalyst precursor bodies may be effected either under inert gas or under an oxidative atmosphere, for example air (mixture of inert gas and oxygen) or else under a reducing atmosphere (for example mixture of inert gas, $NH_3$, CO and/or $H_2$ or methane, acrolein, methacrolein). It will be appreciated that the thermal treatment may also be performed under reduced pressure.

In principle, the thermal treatment of the annular shaped unsupported catalyst precursor bodies may be carried out in highly differing furnace types, for example heatable forced-air chambers, tray furnaces, rotary tube furnaces, belt calciners or shaft furnaces. Preference is given in accordance with the invention to effecting the thermal treatment of the annular shaped unsupported catalyst precursor bodies in a belt calcining apparatus as recommended by DE-A 10046957 and WO 02/24620.

The thermal treatment of the annular shaped unsupported catalyst precursor bodies below 350° C. generally follows the thermal decomposition of the sources of the elemental constituents of the desired annular unsupported catalyst present in the shaped unsupported catalyst precursor bodies. Frequently, this decomposition phase in the process according to the invention proceeds in the course of the heating at temperatures of $\geq 350°$ C.

The annular shaped unsupported catalyst precursor bodies may, as already mentioned, be prepared by generating, from sources of the elemental constituents of the active composition of the desired annular unsupported catalyst, a (very intimate) finely divided shapeable mixture having a composition corresponding to the stoichiometry of the desired active composition and, optionally after adding shaping and/or reinforcing assistants, forming from this an annular shaped unsupported catalyst precursor body (having a curved and/or uncurved top surface) (whose side crushing strength is advantageously ≧10 N and ≦25 N; however, it may also be from 1 N to <10 N, for example from 4 N to 8 N). The geometry of the annular shaped unsupported catalyst precursor body will correspond substantially to that of the desired annular unsupported catalyst.

Useful sources for the elemental constituents of the desired active composition are those compounds which are already oxides and/or those compounds which can be converted to oxides by heating, at least in the presence of oxygen.

In addition to the oxides, useful such starting compounds are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or may be decomposed in the course of later calcining at the latest to give compounds which escape fully in gaseous form may additionally be incorporated into the finely divided shapeable mixture (preferably a dry mixture)).

The preferably intimate mixing of the starting compounds (sources) to prepare the finely divided shapeable mixture in the process according to the invention may be effected in dry or in wet form. When it is effected in dry form, the starting compounds are appropriately used as a finely divided powder (the particle size should advantageously be ≦100 μm, preferably ≦50 μm; in general the number-average largest particle diameter will be ≧10 μm). After any addition of shaping and/or reinforcing assistants, the shaping to the annular shaped unsupported catalyst precursor body may subsequently be effected.

However, preference is given in accordance with the invention to effecting the intimate mixing in wet form. Typically, the starting compounds are mixed together in the form of an aqueous solution and/or suspension. Particularly intimate shapeable mixtures are obtained when the starting materials are exclusively sources of the elemental constituents present in dissolved form. The solvent used is preferably water. Subsequently, the resulting solution or suspension is dried, and the drying process is preferably effected by spray drying with exit temperatures of from 100 to 150° C. The particle size of the resulting spray powder is typically from 20 to 50 μm.

The spray powder may then be compressed (shaped) as such or after addition of shaping and/or reinforcing assistants to give the annular shaped unsupported catalyst precursor bodies. However, the finely divided reinforcing assistants may also be (partly or fully) added in advance of the spray drying. It is also possible in the course of the drying to only partly remove the solvent or suspension agent if the intention is to use it as a shaping assistant.

Instead of shaping the spray powder, optionally after adding shaping and/or reinforcing assistants, directly to the annular shaped unsupported catalyst precursor bodies (having curved and/or uncurved top surface of the rings), it is frequently appropriate to initially carry out an intermediate compaction in order to coarsen the powder (generally to a particle size of from 400 μm to 1 mm). Subsequently, the actual ring shaping is effected with the coarsened powder, and finely divided lubricant may again be added beforehand if required.

A favorable lubricant for such an intermediate compaction (and likewise for the final shaping) has been found to be finely divided graphite from Timcal AG (San Antonio, US) of the TIMREX P44 type, or T44 graphite powder from Lonza, CH-5643 Sins (sieve analysis or laser diffraction: min. 50% by weight <24 μm, max. 10% by weight >24 μm and ≦48 μm, max. 5% by weight >48 μm, BET surface area: from 6 to 13 $m^2/g$). After the completed intermediate compaction, it functions simultaneously as a lubricant in the actual ring shaping (and may, if required, additionally be supplemented as described above). It is found to be favorable when the ash residue of the graphite used (ignite at 815° C. under air) is ≦0.1% by weight.

Such an intermediate compaction for the purpose of particle coarsening may be effected, for example, by means of a compactor from Hosokawa Bepex GmbH (D-74211 Leingarten), of the K 200/100 compactor type. The hardness of the intermediate compactate is frequently already in the region of 10 N. Useful for the ring shaping to the shaped unsupported catalyst precursor body is, for example, a Kilian rotary tableting press (from Kilian in D-50735 Cologne) of the RX 73 or S 100 type. Alternatively, a tableting press from Korsch (D-13509 Berlin) of the PH 800-65 type may be used.

In the preparation of annular unsupported catalysts, it is advantageous (cf. DE-A 4407020, EP-A 835, EP-A 575897, DE-C 3338380, DE-A 10344149), for the preparation of the annular shaped unsupported catalyst precursor body, to preform, as a source of the elements W and Bi, in the absence of the remaining constituents of the active composition I, a mixed oxide II

$$Bi_{a'}W_{b'}O_{x'} \quad (II)$$

where
a'=from 0.01 to 8,
b'=from 0.1 to 30 and
x'=a number which is determined by the valency and frequency of the elements in II other than oxygen, and, after its preformation, as already described, to use it with sources of the remaining constituents of the desired active composition I to generate a finely divided shapeable mixture, in order to shape therefrom, optionally after adding shaping and/or reinforcing assistants, the annular shaped unsupported catalyst precursor body. In such a procedure, it has been found to be advantageous when, in the case that the preparation of the finely divided shapeable mixture is effected in wet form (in suspension), the preformed mixed oxide $Bi_{a'}W_{b'}O_{x'}$, does not go into solution to a significant extent.

Preferred mixed oxides II are those of the stoichiometry $BiWO_6$, $Bi_2W_2O_9$ and $Bi_2W_3O_{12}$.

It will be appreciated that a mixed oxide II may be used as the source of the W and Bi present in the multimetal oxide I only for a portion (for example 25 mol %, or 50 mol %, or 75 mol %, of the particular total amount). However, preference is given to using a mixed oxide II as the source for the entire amount of the W and Bi present in the multimetal oxide I.

The preparation of mixed oxides II may be effected as follows. Water-soluble salts of Bi for example, its nitrates, carbonates, hydroxides or acetates, are mixed in water with tungsten acids or their ammonium salts, the mixture dried (preferably spray-dried) and the dried composition subsequently thermally treated.

The thermally treated composition is subsequently appropriately comminuted (for example in a ball mill or by jet milling) and, from the powder which generally consists of substantially spherical particles and is obtainable in this way, the particle class having a largest particle diameter lying within the desired largest diameter range desired for the active composition I (for example from 1 nm to 100 μm, frequently from 10 nm to 500 nm or from 1 μm to 50 or 25 μm) is separated by classification to be carried out in a manner known per se (for example wet or dry sieving). The thermal treatment in the course of the preparation of mixed oxides II is appropriately effected at temperatures of from 400 to 900° C., preferably from 600 to 900° C. Typically, the thermal treatment is effected in an airstream (for example in a rotary tube furnace as described in DE-A 103 25 487). The duration of the thermal treatment generally extends to a few hours.

According to the invention, the finely divided mixed oxide II is preferably not used as such as the source for preparing a multimetal oxide I. Appropriately in accordance with the invention, from 0.1 to 3% by weight (based on the mass of the finely divided mixed oxide) of finely divided $SiO_2$ (the number-average largest particle diameter of the $SiO_2$ particles which are typically substantially spherical is appropriately from 10 to 50 nm) is preferably mixed with the finely divided mixed oxide II, thus preparing a starting composition 1 which is used as the actual source.

The remaining constituents of the desired active multimetal oxide composition I are then normally used to prepare, starting from sources which are suitable in a manner known per se (cf. EP-A 835 and DE-C 333 8380 and also DE-A 4407020), in an inventively appropriate manner, for example, a very intimate, preferably finely divided dry mixture (for example combining water-soluble salts such as halides, nitrates, acetates, carbonates or hydroxides in an aqueous solution and subsequently, for example, spray-drying the aqueous solution, or suspending water-insoluble salts, for example oxides, in aqueous medium and subsequently, for example, spray-drying the suspension) which is referred to here as starting composition 2. It is essential only that the constituents of the starting composition 2 are either already oxides or compounds which can be converted to oxides by heating, in the absence or presence of oxygen. Subsequently, the starting composition 1 and the starting composition 2 are mixed in the desired ratio, optionally after adding shaping and/or reinforcing assistants, to give the mixture which can be shaped to the annular shaped unsupported catalyst precursor body. The shaping may, as already described, appropriately from an application point of view, be effected by an intermediate compaction stage.

In a less preferred embodiment, the preformed mixed oxide II may also be intimately mixed with sources of the remaining constituents of the desired active composition I in liquid, preferably aqueous, medium. This mixture is subsequently, for example, dried to give an intimate dry mixture and then, as already described, shaped and thermally treated. The sources of the remaining constituents may be dissolved and/or suspended in this liquid medium, whereas the preformed mixed oxide II should be substantially insoluble, i.e. has to be suspended, in this liquid medium.

The preformed mixed oxide II particles are normally present having a substantially unchanged longitudinal dimension established by the classification in the finished annular unsupported catalyst.

In other words, multimetal oxides I are obtainable in this way which contain, for example, at least 25 mol % (preferably at least 50 mol % and more preferably 100 mol %) of the total amount of W present therein in the form of three-dimensional regions of the chemical composition $Bi_{a'}W_{b'}O_{x'}$ which are delimited from the local environment as a consequence of their different chemical composition from their local environment and whose longest diameter is advantageously in the range from 1 nm to 100 μm.

Preference is given in accordance with the invention to the specific surface area of mixed oxides II preformed in this way being from 0.2 to 2 $m^2/g$, preferably from 0.5 to 1.2 $m^2/g$. In addition, the total pore volume of mixed oxides II preformed in this way advantageously results predominantly from micropores.

All data in this document on determinations of specific surface areas or on micropore volumes relates to the determinations to DIN 66131 (determination of the specific surface area of solids by gas adsorption ($N_2$) according to Brunauer-Emmet-Teller (BET)).

All data in this document on determinations of total pore volumes and also of diameter distributions on these total pore volumes relate, unless stated otherwise, to determinations by the mercury porosimetry method employing the Auto Pore 9220 instrument from Micromeritics GmbH, 4040 Neuss, Germany (bandwidth from 30 Å to 0.3 mm).

In principle, the annular unsupported catalysts to be used in accordance with the invention are also obtainable by the preparative processes described in the documents WO 03/039744, EP-A 279374 and EP-A 1340538.

In a corresponding manner, they may also have the physical properties recommended in these documents (specific surface area, total pore volume, contribution of the individual pore diameters to the total pore volume, ratio R ($R=1/(1+V\cdot\rho)$ where V=total pore volume) of apparent mass density to true mass density $\rho$, etc.).

In other words, R for the annular unsupported catalysts to be used in accordance with the invention may either be from 0.25 to 0.55, or >0.55. R is preferably $\leq 0.9$ or $\leq 0.8$ and $\geq 0.6$ or $\geq 0.65$.

Annular unsupported catalysts to be used advantageously in accordance with the invention are also those whose specific surface area S is from 5 to 20, preferably 5 to 15 $m^2/g$, more preferably from 5 to 10 $m^2/g$. According to the invention, the total pore volume V of annular unsupported catalysts which are particularly suitable in accordance with the invention is advantageously in the range from 0.1 to 1 or 0.8 $cm^3/g$, frequently in the range from 0.2 to 0.4 $cm^3/g$.

Advantageously, the different pore diameters in annular unsupported catalysts to be used in accordance with the invention advantageously contribute to the total pore volume as follows (pore distribution A):

pores having a diameter in the range <0.03 μm: $\leq 5\%$ by volume;

pores having a diameter in the range from $\geq 0.03$ to $\leq 0.1$ μm: $\leq 25\%$ by volume;

pores having a diameter in the range from >0.1 to <1 μm: $\geq 70\%$ by volume and pores having a diameter in the range from $\geq 1$ to $\leq 10$ μm: $\leq 10\%$ by volume.

Particularly advantageously, the proportion of the different pore diameters in the total pore volume in annular unsupported catalysts to be used in accordance with the invention has the following distribution (pore distribution B):

pores having a diameter in the range from <0.03 μm: $\geq 0$ and $\leq 5\%$ by volume, preferably $\leq 3\%$ by volume;

pores having a diameter in the range from $\geq 0.03$ to $\leq 0.1$ μm: $\geq 3$ or $\geq 5$ and $\leq 20$ or $\leq 15\%$ by volume;

pores having a diameter in the range from >0.1 to <1 μm: $\geq 75$ or $\geq 80$ and $\leq 95$ or $\leq 90\%$ by volume;

pores having a diameter in the range from $\geq 1$ μm to $\leq 10$ μm: $\geq 0$ and $\leq 5\%$ by volume, preferably $\leq 3\%$ by volume.

In addition, it is favorable for annular unsupported catalysts to be used in accordance with the invention when that pore diameter which makes the greatest percentage contribution to the total pore volume V, $d^{max}$, is from 0.3 to 0.8 μm, particularly advantageously from 0.4 to 0.7 μm and very particularly advantageously from 0.5 to 0.6 μm.

For the process according to the invention, particular preference is given to using those annular unsupported catalysts for which, simultaneously:

S=from 5 to 10 m$^2$/g, preferably from 5 to 15 m$^2$/g, more preferably from 5 to 10 M$^2$/g;

V=from 0.1 to 1 cm$^3$/g, preferably from 0.1 to 0.8 cm$^3$/g, more preferably from 0.2 to 0.4 cm$^3$/g; and pore distribution=pore distribution A or pore distribution B.

In addition, it is advantageous in accordance with the invention when, simultaneously:

$d^{max}$=from 0.3 to 0.8 μm, preferably from 0.4 to 0.7 μm and more preferably from 0.5 to 0.6 μm.

In a manner which is remarkable in the context of the invention, pores within the pore diameter range from >0.1 to <1 μm promote in particular the selectivity of acrolein formation.

In contrast, pores within the pore diameter range from 0.01 to 0.1 μm, if anything, promote the selectivity of acrylic acid by-production.

With increasing side crushing strength of the annular shaped unsupported catalyst precursor body, the pore diameters in the resulting unsupported catalyst ring are generally shifted to larger values. At the same time, the side crushing strength of the resulting annular unsupported catalyst normally shifts to higher values. The side crushing strength of the resulting unsupported catalyst is generally less than the side crushing strength of the corresponding annular shaped unsupported catalyst precursor body.

Typically, the side crushing strengths of annular unsupported catalysts which are suitable in accordance with the invention are from 5 to 15 N, frequently from 8 to 11 N. Annular unsupported catalysts to be used in accordance with the invention are favorable in particular when the aforementioned side crushing strengths and simultaneously the aforementioned combinations of S, V, pore distribution A or pore distribution B and also in some cases $d^{max}$ are present.

The process according to the invention for the partial, heterogeneously catalyzed gas phase oxidation of propene to acrolein may otherwise be carried out as described in the documents WO 00/53557, WO 00/53558, DE-A 19910506, EP-A 1106598, WO 01/36364, DE-A 19927624, WO 00/53557, DE-A 19948248, DE-A 19948523, DE-A 19948241, EP-A 700714, DE-A 10313213, DE-A 10313209, DE-A 10232748, DE-A 10313208, WO 03/038744, EP-A 279374, DE-A 3338380, DE-A 3300044, EP-A 575897, DE-A 4407020, DE-A 10344149, DE-A 10351269 and DE-A 10350812, and the fixed catalyst bed may comprise, for example, only annular unsupported catalysts to be used in accordance with the invention or annular unsupported catalysts diluted with inert shaped bodies. In the latter case, the fixed catalyst bed, advantageously in accordance with the invention, is generally configured in such a way that its volume-specific activity increases continuously, sharply and/or stepwise in the flow direction of the reaction gas mixture.

The advantageousness of the annular unsupported catalysts to be used in accordance with the invention is exhibited in particular when the hourly space velocity on the fixed catalyst bed of propene is ≧130 1 (STP)/1·h, or ≧140 1 (STP)/1·h, or ≧150 1 (STP)/1·h, or ≧160 1 (STP)/1·h. Normally, the aforementioned hourly space velocity on the fixed catalyst bed will be ≦600 1 (STP)/1·h, frequently ≦500 1 (STP)/1·h, in many cases ≦400 1 (STP)/1·h or ≦350 1 (STP)/1·h. Propene hourly space velocities on the fixed catalyst bed in the range from 160 1 (STP)/1·h to 300 or 250 or 200 1 (STP)/1·h are particularly typical.

It will be appreciated that the process according to the invention may also be operated at noninventive propene hourly space velocities on the fixed catalyst bed to be used of ≦120 1 (STP)/1·h, or ≦110 1 (STP)/1·h, or ≦100 1 (STP)/1·h. However, such noninventive propene hourly space velocities will generally be at values of ≧60 1 (STP)/1·h, or ≧80 1 (STP)/1·h.

In this document (as is generally customary), the "propene hourly space velocity" on the fixed catalyst bed refers to the amount of propene in liters at STP (=1 (STP); the volume in liters that the appropriate amount of propene would occupy under standard conditions, i.e. at 25° C. and 1 bar) which is conducted as a constituent of the starting reaction gas mixture per hour through one liter of fixed catalyst bed. In this context, upstream and/or downstream beds of pure inert material are not considered to belong to the fixed catalyst bed. Hourly space velocities on the fixed catalyst bed of starting reaction gas mixture are understood in a corresponding manner; "propene" merely has to be replaced by "starting reaction gas mixture".

In principle, the hourly space velocity on the fixed catalyst bed of propene in the process according to the invention may be adjusted using two adjusting screws:

a) the hourly space velocity on the fixed catalyst bed of starting reaction gas mixture and/or b) the content in the starting reaction gas mixture of propene.

The process according to the invention is suitable both when, at propene hourly space velocities on the fixed catalyst bed of ≧120 1 (STP)/1·h, the hourly space velocity is adjusted using the aforementioned adjusting screw a), and when the hourly space velocity is adjusted using the aforementioned adjusting screw b). In general, a high-load setting using the adjusting screw a) is found to be advantageous, since the associated comparatively low partial propene pressure is accompanied by a relatively low residence time in the catalyst structure and simultaneously makes it difficult for the active centers on the catalyst surface to be blocked. In addition, such a procedure is accompanied by more advantageous radial and axial transportation away of heat.

In the process according to the invention, the propene fraction in the starting reaction gas mixture will generally (i.e. essentially irrespective of the hourly space velocity) be from 4 to 20% by volume, frequently from 5 to 15% by volume, or from 5 to 12% by volume, or from 5 to 8% by volume (based in each case on the total volume). Favorable propene fractions in accordance with the invention are also the ranges having the same basis of from 7 to 15% by volume or from 8 to 12% by volume, or from 9 to 11% by volume, and from 5 to 8% by volume.

Frequently, the process of the partial oxidation catalyzed by the annular unsupported catalysts obtainable in accordance with the invention will be carried out (essentially irrespective of the hourly space velocity) at a propene: oxygen: inert gases (including steam) volume ratio in the starting reaction gas mixture of from 1:(1.0 to 3.0):(3 to 30), preferably 1:(1.5 to 2.3):(10 to 15).

In other words the molar $O_2$:$C_3H_6$ ratio in the starting reaction gas mixture will generally be ≦3.

Inert gases refer to those gases of which at least 95 mol %, preferably at least 98 mol %, remains chemically unchanged in the course of the partial oxidation.

In the above-described starting reaction gas mixtures, the inert gas may consist of ≧20% by volume, or ≧30% by volume, or ≧40% by volume, or ≧50% by volume, or ≧60% by volume, or ≧70% by volume or ≧80% by volume, or ≧90% by volume or ≧95% by volume, of molecular nitrogen.

However, the inert diluent gas may also consist of, for example, from 2 to 35 or 20% by volume of $H_2O$ and from 65 to 98% by volume of $N_2$.

However, when the hourly space velocities on the fixed catalyst bed of propene are ≧250 1 (STP)/1·h, it is recommended to use inert diluent gases such as propane, ethane, methane, pentane, butane, $CO_2$, CO, steam and/or noble gases for the starting reaction gas mixture. Generally, these inert gases and their mixtures may also be used even at lower inventive hourly space velocities on the catalyst charge of the organic compound to be partially oxidized. Cycle gas may also be used as a diluent gas. Cycle gas refers to the residual gas which remains when the target compound is substantially selectively removed from the product gas mixture of the partial oxidation. It has to be taken into account that the inventive partial oxidation to acrolein using the annular unsupported catalysts to be used in accordance with the invention may only be the first stage of a two-stage partial oxidation of propene to acrylic acid as the actual target compound, so that the cycle gas is then not usually formed until after the second stage. In such a two-stage partial oxidation, the product gas mixture of the first stage is generally fed as such, optionally after cooling and/or secondary oxygen addition, to the second partial oxidation stage.

It is essential to the invention merely that the starting reaction gas mixture contains carbon dioxide and saturated hydrocarbons together in a total amount of ≦15 mol % (or 15% by volume), preferably of ≦10 mol % and more preferably ≦5 mol % or ≦3 mol %.

In the inventive partial oxidation of propene to acrolein using the annular unsupported catalysts to be used in accordance with the invention, a typical composition of the starting reaction gas mixture (irrespective of the hourly space velocity selected) may comprise, for example, the following components:

from 6 to 6.5% by volume of propene,
from 3 to 3.5% by volume of $H_2O$,
from 0.3 to 0.5% by volume of CO,
from 0.8 to 1.2% by volume of $CO_2$,
from 0.025 to 0.04% by volume of acrolein,
from 10.4 to 10.7% by volume of $O_2$ and
as the remainder ad 100%, (essentially) molecular nitrogen, or: 5.4% by volume of propene,
10.5% by volume of oxygen,
1.2% by volume of $CO_x$,
81.3% by volume of $N_2$ and
1.6% by volume of $H_2O$.

However, the starting reaction gas mixture may also have the following composition:

from 7 to 15% by volume of propene,
from 4 to 30% by volume (frequently from 6 to 15% by volume) of water,
from ≧0 to 10% by volume preferably from ≧0 to 5% by volume) of constituents other than propene, water, oxygen and nitrogen, and sufficient molecular oxygen that the molar ratio of molecular oxygen present to molecular propene present is from 1.5 to 2.5, and, as the remainder up to 100% by volume of the total amount, (essentially) molecular nitrogen.

Another possible starting reaction gas mixture composition may comprise:

6.0% by volume of propene,
60% by volume of air and
34% by volume of $H_2O$.

Alternatively, starting reaction gas mixtures of the composition according to Example 1 of EP-A 990 636, or according to Example 2 of EP-A 990 636, or according to Example 3 of EP-A 1 106 598, or according to Example 26 of EP-A 1 106 598, or according to Example 53 of EP-A 1 106 598, may also be used.

Further starting reaction gas mixtures which are suitable in accordance with the invention may lie within the following composition framework:

from 7 to 11% by volume of propene,
from 6 to 12% by volume of water,
from ≧0 to 5% by volume of constituents other than propene, water, oxygen and nitrogen,
sufficient molecular oxygen that the molar ratio of oxygen present to molecular propene present is from 1.6 to 2.2, and
as the remainder up to 100% by volume of the total amount, (essentially) molecular nitrogen.

The reaction temperature for the propene partial oxidation (i.e. the temperature of the fixed catalyst bed) when the annular unsupported catalysts to be employed in accordance with the invention are used is frequently from 150 to 450° C., preferably in the range from 300 to 400° C. and more preferably from 300 to 380° C.

The reaction pressure for the aforementioned partial oxidation is generally from 0.5 or 1.5 to 3 or 4 bar.

The total hourly space velocity on the fixed catalyst bed of starting reaction gas mixture in the inventive partial oxidations typically amounts to from 1000 to 10 000 1 (STP)/1·h, usually to from 1500 to 5000 1 (STP)/1·h and often to from 2000 to 4000 1 (STP)/1·h.

The propene to be used in the starting reaction gas mixture is in particular polymer-grade propene and chemical-grade propene, as described, for example, in DE-A 10232748.

The oxygen source used is normally air.

In the simplest case, the inventive partial oxidation employing the annular unsupported catalysts to be used in accordance with the invention may be carried out, for example, in a one-zone multiple catalyst tube fixed bed reactor, as described by DE-A 44 31 957, EP-A 700 714, WO 03/057653, WO 03/055835, WO 03/059857, WO 03/076373 and EP-A 700 893.

Customarily, the catalyst tubes in the aforementioned tube bundle reactors are manufactured from ferritic steel and typically have a wall thickness of from 1 to 3 mm. Their internal diameter is generally from 20 to 30 mm, frequently from 22 to 26 mm. A typical catalyst tube length is, for example, 3.20 m. It is appropriate from an application point of view for the number of catalyst tubes accommodated in the tube bundle vessel to be at least 5000, preferably at least 1000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally arranged in homogeneous distribution, and the distribution is appropriately selected in such a way that the separation of the central internal axes of immediately adjacent catalyst tubes (known as the catalyst tube pitch) is from 35 to 45 mm (cf. EP-B 468 290).

However, the partial oxidation may also be carried out in a multizone (for example "two") multiple catalyst tube fixed bed reactor, as recommended by DE-A 19948523, DE-A 199

10 506, DE-A 10313213, DE-A 10313208 and EP-A 1106 598, especially at particularly elevated propene hourly space velocities on the fixed catalyst bed (for example at $\geqq 160$ l (STP)l·h). A typical catalyst tube length in the case of a two-zone multiple catalyst tube fixed bed reactor is 3.50 m. Everything else is substantially as described for the one-zone multiple catalyst tube fixed bed reactor. Around the catalyst tubes, within which the catalyst charge is disposed, a heat exchange medium is conducted in each heating zone. Suitable such media are, for example, melts of salts such as potassium nitrate, potassium nitrite, sodium nitrite and/or sodium nitrate, or of low-melting metals such as sodium, mercury and also alloys of different metals. The flow rate of the heat exchange medium within the particular heating zone is generally selected in such a way that the temperature of the heat exchange medium increases from the entry point into the temperature zone to the exit point from the temperature zone by from 0 to 15° C., frequently from 1 to 10° C., or from 2 to 8° C., or from 3 to 6° C.

The entrance temperature of the heat exchange medium which, viewed over the particular heating zone (including the one-zone in the one-zone multiple catalyst tube fixed bed reactor), may be conducted in cocurrent or in countercurrent to the reaction gas mixture (particular preference being given in accordance with the invention to the cocurrent method), is preferably selected as recommended in the documents EP-A 1 106 598, DE-A 19948523, DE-A 19948248, DE-A 10313209, EP-A 700 714, DE-A 10313208, DE-A 10313213, WO 00/53557, WO 00/53558, WO 01/36364, WO 00/53557 and also the other documents cited as prior art in this document. Within the heating zone, the heat exchange medium is preferably conducted in a meandering manner. In general, the multiple catalyst tube fixed bed reactor additionally has thermal tubes for determining the gas temperature in the catalyst bed. Appropriately, the internal diameter of the thermal tubes and the diameter of the internal accommodating sleeve for the thermoelement are selected in such a way that the ratio of volume developing heat of reaction to surface area removing heat for the thermal tube and working tubes is the same (c.f. EP-A 873783, WO 03-076373 and EP-A 1270065).

The pressure drop for working tubes and thermal tube, based on the same GHSV, should be the same. The pressure drop may be equalized in the case of the thermal tube by adding spalled catalyst rings to the annular unsupported catalysts. This equalization is appropriately effected homogeneously over the entire thermal tube length.

To prepare the fixed catalyst bed in the catalyst tubes in the process according to the invention, as already mentioned, it is possible to only use annular unsupported catalysts to be used in accordance with the invention, or, for example, also substantially homogeneous mixtures of annular unsupported catalysts to be used in accordance with the invention and shaped bodies which have no active composition and behave substantially inertly with respect to the heterogeneously catalyzed partial gas phase oxidation of propene to acrolein. Useful materials for such inert shaped bodies include, for example, porous or nonporous aluminum oxides, silicon dioxide, thorium dioxide, zirconium dioxide, silicon carbide, silicates such as magnesium or aluminum silicate or steatite (for example of the C220 type from CeramTec, Germany).

The geometry of such inert shaped diluent bodies may in principle be as desired. In other words, they may be, for example, spheres, polygons, solid cylinders or else, like the shaped catalyst bodies, rings. Frequently, the inert shaped diluent bodies selected will be those whose geometry corresponds to that of the annular unsupported catalysts to be diluted with them. However, along the fixed catalyst bed, the annular geometry may also be changed. In a less preferred procedure, the active composition of the annular unsupported catalysts may also be changed along the fixed catalyst bed, as long as it remains a constituent of the general formula I.

Quite generally, as already mentioned, the fixed catalyst bed is advantageously configured in such a way that the volume-specific (i.e. normalized to the unit of the volume) activity either remains constant or increases (continuously, sharply or stepwise) in the flow direction of the reaction gas mixture.

A reduction in the volume-specific activity may be achieved in a simple manner, for example, by homogeneously diluting a basic amount of annular unsupported catalysts prepared uniformly in accordance with the invention with inert shaped diluent bodies. The higher the proportion of the shaped diluent bodies is selected, the lower the active composition, i.e. catalyst activity, present in a certain volume of the charge. However, a reduction can also be achieved by changing the geometry of the annular unsupported catalysts to be used in accordance with the invention in such a way that the amount of active composition present in the unit of the total ring volume (including the ring orifice) becomes smaller.

For the inventive heterogeneously catalyzed gas phase partial oxidation using the annular unsupported catalysts to be used in accordance with the invention, the fixed catalyst bed is preferably either configured uniformly with only one unsupported catalyst ring over the entire length or structured as follows. Initially to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of the fixed catalyst bed, a substantially homogeneous mixture of shaped diluent bodies and annular unsupported catalyst to be used in accordance with the invention (both preferably having substantially the same geometry), the proportion by weight of the shaped diluent bodies (the mass densities of shaped catalyst bodies and of shaped diluent bodies generally differing only slightly) being normally from 5 to 40% by weight, or from 10 to 40% by weight, or from 20 to 40% by weight, or from 25 to 35% by weight. Downstream of this first charge section, there is then advantageously, up to the end of the length of the fixed catalyst bed (i.e., for example, to a length of from 2.00 to 3.00 m, preferably from 2.50 to 3.00 m), either a bed of the annular unsupported catalyst to be used in accordance with the invention which is diluted only to a lesser extent (than in the first section), or, most preferably, an unaccompanied (undiluted) bed of the same annular unsupported catalyst which has also been used in the first section. Of course, a constant dilution may also be selected over the entire charge. Charging may also be effected in the first section using only an annular unsupported catalyst to be used in accordance with the invention and having lower active composition density based on its space demands, and, in the second section, using an annular unsupported catalyst to be used in accordance with the invention having higher active composition density based on its space demands (for example 6.5 mm×3 mm×4.5 mm [E×L×I] in the first section, and 5×2×2 mm in the second section).

Overall, in an inventive partial oxidation of propene to acrolein, the fixed catalyst bed, the starting reaction gas mixture, the hourly space velocity and the reaction temperature (temperature of the fixed catalyst bed) are generally selected in such a way that, on single pass of the reaction gas mixture through the fixed catalyst bed, a conversion of the propene to be partially oxidized of at least 90 mol %, or at least 92 mol %, preferably of at least 95 mol % or at least 97 mol %, results. The selectivity of acrolein formation will regularly be ≧80 mol %, or ≧82 mol %, or ≧84 mol %, or ≧85 mol %, or ≧86 mol %, or ≧87 mol %. Of course, very low hotspot temperatures are the result. At the same time, an increased selectivity of target product formation results.

Finally, it should be emphasized that the annular unsupported catalysts to be used in accordance with the invention also have advantageous fracture behavior in the course of reactor charging. Their pressure drop behavior is also advantageous. Otherwise, the annular unsupported catalysts to be used in accordance with the invention are quite generally suitable as catalysts having increased activity and selectivity for catalytic partial oxidations in the gas phase of organic compounds such as lower (for example containing from 3 to 6 (i.e. 3, 4, 5, or 6) carbon atoms) alkanes, alkanols, alkanals, alkenes and alkenals to olefinically unsaturated aldehydes and/or carboxylic acids, and also the appropriate nitriles (ammoxidation, in particular of propene to acrylonitrile and of 2-methylpropene or tert-butanol (or its methyl ether) to methacrylonitrile) and also for catalytic oxidative dehydrogenations in the gas phase of organic compounds (for example containing 3, 4, 5, or 6 carbon atoms). In the case of methacrolein as the target compound, the procedure may be that of DE-A 4407020.

The bismuth content of the active compositions obtainable in accordance with the invention may also be adjusted as described in DE-A 100 63 162. In this method, a solution or suspension is generated from starting compounds of the elemental constituents of the desired active composition, said solution or suspension containing the total amount of elemental constituents other than Bi required to prepare the active composition, but only a portion of the Bi required to prepare the active composition, the solution or suspension is dried to obtain a dry mass and the remaining amount of Bi additionally required to prepare the active composition is incorporated into this dry mass in the form of a starting compound of Bi, as described in DE-A 100 63 162, to obtain a shapeable mixture (for example as in the example of DE-A 100 63 162), the shapeable mixture is shaped to an annular shaped unsupported catalyst body in the inventive manner (optionally after adding shaping and/or reinforcing assistants), and this is then converted to the desired annular unsupported catalyst by thermal treatment (for example as in the example of DE-A 100 63 162).

An advantage of the inventive procedure is also that, in the event of change in the propene load on the fixed catalyst bed, necessary as a consequence of varying market demand for the target product, such adjustments are possible without there having to be accompanying marked changes in the temperature of the fixed catalyst bed based on constant propene conversion on single pass of the reaction gas mixture. This considerably eases the plant design.

The start-up of a fresh fixed catalyst bed (or of a freshly regenerated fixed catalyst bed) comprising annular unsupported catalysts to be used in accordance with the invention may be effected as described in DE-A 10337788. In general, activity and selectivity of the target product formation initially increase with the operating time of the catalyst charge. This conditioning may be accelerated by carrying it out at substantially uniform conversion under increased hourly space velocity on the catalyst charge of starting reaction gas mixture, and, after substantially completed conditioning, reducing the hourly space velocity to its target value.

The regeneration of a fixed catalyst bed operated in accordance with the invention can be effected as described in the documents DE-A 10351269, DE-A 10350812, EP-A 169449, EP-A 614872 and EP-A 339119.

Finally, it should be emphasized that the process according to the invention can also be carried out in a noninventive manner using unsupported catalysts composed of multimetal oxides of the general formula I but having a geometry different to an annular geometry in accordance with DE-A 10101695, in which case the propene hourly space velocity may be ≧120 l (STP)/l·h or <120 l (STP)/l·h.

Particularly preferred unsupported catalyst geometries are in particular those of FIG. 1A and FIG. 2A of DE-A 10101695.

EXAMPLE AND COMPARATIVE EXAMPLE

A) Preparation of an Annular Comparative Unsupported Catalyst CUC Having the Following Stoichiometry CS of the Active Composition:

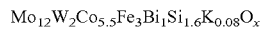

$Mo_{12}W_2Co_{5.5}Fe_3Bi_1Si_{1.6}K_{0.08}O_x$

1. Preparation of a Starting Composition 1

209.3 kg of tungstic acid (72.94% by weight of W) were stirred in portions into 775 kg of an aqueous bismuth nitrate solution in nitric acid (11.2% by weight of Bi; free nitric acid from 3 to 5% by weight; mass density: 1.22 to 1.27 g/ml) at 25° C. The resulting aqueous mixture was subsequently stirred at 25° C. for a further 2 h and subsequently spray-dried.

The spray-drying was effected in a rotating disk spray tower in countercurrent at a gas inlet temperature of 300±10° C. and a gas outlet temperature of 100±10° C. The resulting spray powder (particle size a substantially uniform 30 μm) which had an ignition loss of 12% by weight (ignite at 600° C. under air for 3 h) was subsequently converted to a paste in a kneader using 16.8% by weight (based on the powder) of water and extruded by means of an extruder (rotational moment: ≦50 Nm) to extrudates of diameter 6 mm. These were cut into sections of 6 cm, dried under air on a 3-zone belt dryer at a residence time of 120 min at temperatures of 90-95° C. (zone 1), 115° C. (zone 2) and 125° C. (zone 3), and then thermally treated at a temperature in the range from 780 to 810° C. (calcined; in a rotary tube oven flowed through by air (0.3 mbar of reduced pressure, capacity 1.54 m³, 200 m³ (STP) of air/h)). When precisely adjusting the calcination temperature, it is essential that it has to be directed to the desired phase composition of the calcination product. The desired phases are WO₃ (monoclinic) and Bi₂W₂O₉; the presence of γ-Bi₂WO₆ (Russellite) is undesired. Therefore, should the compound γ-Bi₂WO₆ still be detectable by a reflection at a reflection angle of 2θ=28.4° (CuKα radiation) in the x-ray powder diffractogram after the calcination, the preparation has to be repeated and the calcination temperature increased within the temperature range specified or the residence time increased at constant calcination temperature, until the disappearance of the reflection is achieved. The preformed calcined mixed oxide obtained in this way was ground so that the $X_{50}$ value (cf. Ullmann's Encyclopedia of Industrial Chemistry, 6$^{th}$ Edition (1998) Electronic Release, Chapter 3.1.4 or DIN 66141) of the resulting particle size was 5 mm. The ground material was then mixed with 1% by weight (based on the ground material) of finely divided SiO₂ from Degussa of the Sipernat® type (bulk density 150 g/l; $X_{50}$ value of the SiO₂ particles was 10 μm, the BET surface area was 100 m²/g).

2. Preparation of a Starting Composition 2

A solution A was prepared by dissolving 213 kg of ammonium heptamolybdate tetrahydrate (81.5% by weight of MoO₃) at 60° C. with stirring in 600 l of water and the resulting solution was admixed while maintaining the 60° C. and stirring with 0.97 kg of an aqueous potassium hydroxide solution (46.8% by weight of KOH) at 20° C.

A solution B was prepared by introducing 116.25 kg of an aqueous iron(III) nitrate solution (14.2% by weight of Fe) at 60° C. into 262.9 kg of an aqueous cobalt(II) nitrate solution (12.4% by weight of Co). Subsequently, while maintaining the 60° C., solution B was continuously pumped into the initially charged solution A over a period of 30 minutes. Subsequently, the mixture was stirred at 60° C. for 15 minutes. 19.16 kg of a Ludox silica gel from Dupont (46.80% by weight of SiO₂, density: from 1.36 to 1.42 g/ml, pH from 8.5 to 9.5, max. alkali content 0.5% by weight) were then added to the resulting aqueous mixture, and the mixture was stirred afterward at 60° C. for a further 15 minutes.

Subsequently, the mixture was spray-dried in countercurrent in a rotating disk spray tower (gas inlet temperature: 400±10° C., gas outlet temperature: 140±5° C.). The resulting spray powder had an ignition loss of approx. 30% by weight (ignite under air at 600° C. for 3 h) and a substantially uniform particle size of 30 μm.

3. Preparation of the Multimetal Oxide Active Composition

The starting composition 1 was mixed homogeneously with the starting composition 2 in the amounts required for a multimetal oxide active composition of the comparative stoichiometry $$Mo_{12}W_2Co_{5.5}Fe_3Bi_1Si_{1.6}K_{0.08}O_x$$

in a mixer having bladed heads. Based on the aforementioned overall composition, an additional 1% by weight of finely divided graphite from Timcal AG (San Antonio, US) of the TIMREX P44 type (sieve analysis: min. 50% by weight <24 mm, max. 10% by weight ≧24 μm and ≦48 μm, max. 5% by weight >48 μm, BET surface area: from 6 to 13 m²/g) was mixed in homogeneously. The resulting mixture was then conveyed in a compactor (from Hosokawa Bepex GmbH, D-74211 Leingarten) of the K200/100 compactor type having concave, fluted smooth rolls (gap width: 2.8 mm, sieve width: 1.0 mm, lower particle size sieve width: 400 μm, target compressive force: 60 kN, screw rotation rate: from 65 to 70 revolutions per minute). The resulting compactate had a hardness of 10 N and a substantially uniform particle size of from 400 μm to 1 mm.

The compactate was subsequently mixed with, based on its weight, a further 2% by weight of the same graphite and subsequently compressed in a Kilian rotary tableting press of the Rx 73 type from Kilian, D-50735 Cologne, under a nitrogen atmosphere to give an annular shaped unsupported catalyst precursor body of geometry (E×L×I) 6 mm×3 mm×4 mm having a side crushing strength of 16.3 N.

For the final thermal treatment, 1000 g of the shaped unsupported catalyst precursor bodies were heated in a muffle furnace flowed through by air (capacity 60 l, 1 l/h of air per gram of shaped unsupported catalyst precursor body) initially from room temperature (25° C.) to 190° C. at a heating rate of 180° C./h. This temperature was maintained for 1 h and then increased to 210° C. at a heating rate of 60° C./h. The temperature of 210° C. was in turn maintained over 1 h before it was increased to 230° C. at a heating rate of 60° C./h. This temperature was likewise maintained for 1 h before it was increased to 265° C., again at a heating rate of 60° C./h. The temperature of 265° C. was subsequently likewise maintained over 1 h. Afterward, the furnace was initially cooled to room temperature and the decomposition phase thus substantially completed. The furnace was then heated to 465° C. at a heating rate of 180° C./h and this calcination temperature maintained over 4 h.

The following annular comparative unsupported catalyst was obtained from the annular shaped unsupported catalyst precursor body:

| | |
|---|---|
| specific surface area S: | 9.61 m²/g. |
| total pore volume V: | 0.22 cm³/g. |
| $d^{max}$ [μm]: | 0.30. |
| R: | 0.68. |

Percentage of that pore diameter in the total pore volume whose diameter is >0.1 and <1 μm: $V_1^{0.1}\% = 70$.

FIG. 1 also shows the pore distribution of the comparative annular unsupported catalyst CS. On the abscissa is plotted the pore diameter in μm (logarithmic scale). On the left ordinate is plotted the logarithm of the different contribution in ml/g of the particular pore diameter to the total pore volume (+ curve). The maximum indicates the pore diameter having the greatest contribution to the total pore volume. On the right ordinate is plotted, in ml/g, the integral over the individual contributions of the individual pore diameters to the total pore volume (O curve). The endpoint is the total pore volume.

B) Preparation of an Inventive Annular Unsupported Catalyst IUC Having the Following Inventive Stoichiometry IS of the Active Composition:

$$Mo_{12}W_2Co_7Fe_3Bi_1Si_{1.6}K_{0.08}O_y$$

The preparation was as for the comparative unsupported catalyst CUC, but with the difference that, in the preparation of the solution B, the amount of the aqueous cobalt(II) nitrate solution was increased from 262.9 kg to 334.6 kg. In addition, the starting composition 1 was mixed with the starting composition 2 in the amounts required for a multimetal oxide active composition of the inventive stoichiometry $$Mo_{12}W_2Co_7Fe_3Bi_1Si_{1.6}K_{0.08}O_y$$

The physical properties of the resulting inventive annular (6 mm×3 mm×4 mm) unsupported catalyst IUC (S, V, $d^{max}$, R, $V_1^{0.1}\%$) could not be distinguished from those of the annular comparative unsupported catalyst CUC within the reproducibility.

Instead of carrying out the thermal treatment as in the preparation of the comparative unsupported catalyst CUC, it can also be carried out both in the preparation of CUC and of IUC by means of a belt calcining apparatus as described in Example 1 of DE-A 10046957 (except that the bed height in the decomposition (chambers 1 to 4) is advantageously 44 mm at a residence time per chamber of 1.46 h, and in the calcination (chambers 5 to 8), it is advantageously 130 mm at a residence time of 4.67 h); the chambers have a surface area (at a uniform chamber length of 1.40 m) of 1.29 m² (decomposition) and 1.40 m² (calcination) and are flowed through from below through the coarse-mesh belt by 75 m³ (STP)/h of forced air which is aspirated by means of rotating ventilators. Within the chambers, the temporal and local deviation of the temperature from the target value is always ≦2° C. Otherwise, the procedure is as described in Example 1 of DE-A 10046957. The resulting annular unsupported catalysts, like the annular unsupported catalysts CUC and IUC, may be used for the catalytic partial oxidations in the gas phase of propene to acrolein described hereinbelow under C).

As a further alternative, the thermal treatment may be carried out in a forced-air oven (for example in a KA-040/006-08 EW.OH laboratory chamber oven from Elino or a K 750 from Heraeus) in such a way that the oven is heated to 270° C. within 6 h and the temperature of 270° C. is subsequently maintained until the forced air is free of nitrous gases. Subsequently, the oven is heated to a temperature of from 430° C. to 460° C. (preferably to 438° C.) within 1.5 h and this temperature is maintained for 10 h. The air flushing stream is 800 l (STP)/h. 1000 g of annular shaped unsupported catalyst precursor bodies are charged in a bed height of approx. 4 cm into a rectangular wire basket (10 cm high, 14 cm×14 cm surface area). The remaining surface area of the carrier basket is covered in a corresponding bed height with steatite rings of the same geometry (as always in the examples and comparative examples of the C220 type from Ceram Tec, Germany).

The resulting annular unsupported catalysts may, like the annular unsupported catalysts CUC and IUC, be used in the catalytic partial oxidations in the gas phase described by way of example under C).

C) Testing of the Annular Unsupported Catalysts CUC and IUC Prepared in A) and B) for a Heterogeneously Catalyzed Partial Oxidation of Propene to Acrolein 1. Experimental Arrangement A reaction tube (V2A steel; external diameter 30 mm, wall thickness 2 mm, internal diameter 26 mm, length 320 cm, a thermal tube (external diameter 4 mm) centered in the middle of the reaction tube to accommodate a thermoelement by which the temperature in the reaction tube can be determined over its entire length.

Charging was effected as follows in the flow direction:
Section 1: length 50 cm
    steatite rings of geometry 7 mm×7 mm×4 mm (external diameter×length×internal diameter) as a preliminary bed.
Section 2: length 270 cm
    catalyst charge of the annular unsupported catalysts CUC and IUC.

The reaction tube was heated by means of a salt bath pumped in countercurrent.

2. Experimental Procedure

The experimental arrangement described, in each case freshly prepared, was in each case charged continuously with a charge gas mixture (starting reaction gas mixture) of the composition
    5.4% by volume of propene (chemical-grade propylene),
    10.5% by volume of oxygen,
    1.2% by volume of $CO_x$,
    81.3% by volume of $N_2$ and
    1.6% by volume of $H_2O$, and the thermostating of the reaction tube at a given hourly space velocity PHSV (l (STP)/l·h) on the fixed catalyst bed of propene present in the starting reaction gas mixture was effected in such a way that the propene conversion C (mol %) in single pass of the starting reaction gas mixture through the reaction tube was continuously about 95 mol %.

The table which follows shows the hotspot temperature ($T^{HS}$ (° C.)) which becomes established at the selected propene hourly space velocity of 150 l (STP)/l·h and also the targeted selectivity $S^A$ of acrolein formation in mol % and based on propene converted in single pass, as a function of the selected fixed catalyst bed.

The results reported are always based on the end of an operating time of 120 h.

In addition, the table shows by how many ° C. the salt bath temperature had to be reduced ($\Delta T^S$) in order to maintain the propene conversion in the event of a reduction (under otherwise constant conditions) of PHSV from 150 l (STP)/l·h to 100 l (STP)/l·h.

TABLE

|  | $T^{HS}$ (° C.) | $S^A$ (mol %) | $\Delta T^S$ (° C.) |
| --- | --- | --- | --- |
| CUC | 424 | 87.9 | 27 |
| IUC | 392 | 88.3 | 7 |

The results show that all the advantages are on the side of the IUC fixed catalyst bed. The selectivity of acrylic acid by-production was in all cases about 8.5 mol % (based on propene converted).

The above-described experimental procedure may also be carried out in a corresponding manner using a catalyst charge whose section 2 is configured as follows (in each case in flow direction):

I. initially to length 100 cm, a homogeneous mixture of 65% by weight of IUC and 35% by weight of steatite rings (5 mm×3 mm×2 mm); then to length 170 cm a homogeneous mixture of 90% by weight of IUC and 10% by weight of steatite rings (5 mm×3 mm×2 mm);

or

II. initially to length 100 cm, a homogeneous mixture of 70% by weight of IUC and 30% by weight of steatite rings (5 mm×3 mm×2 mm);
then, to length 170 cm, IUC.

The salt bath temperature is always selected such that C-propene=95 mol % on single pass.

All examples and comparative examples described may also be carried out using a starting reaction gas mixture which, instead of 5.4% by volume of propene, contains 6.7% by volume of propene, and, instead of 81.3% by volume of $N_2$, 80% by volume of $N_2$.

In the inventive and comparative examples of the documents DE-A 10313210, DE-A 10313213, DE-A 10313212 and DE-A 10313208, the annular catalyst IUC may also replace the annular unsupported catalyst used in these documents.

U.S. Provisional Patent Application No. 60/520,660, filed on Nov. 18, 2003, is incorporated into the present application by literature reference.

With regard to the abovementioned teachings, numerous alterations and deviations from the present invention are possible. It may therefore by assumed that, within the scope of the appended claims, the invention may be performed differently to the way specifically described herein.

We claim:

1. A catalyst comprising a metal oxide of the general formula I,

$$Mo_{12}W_aCo_bFe_cBi_dSi_eK_fO_n \quad (I)$$

where
    a=from ≧1 to ≦3,
    b=from ≧3 to ≦8,
    c=from ≧1 to ≦4,
    d=from ≧0.5 to ≦1.5,
    e=from ≧0 to ≦10,
    f=from ≧0 to ≦0.2 and
    n=a number which is determined by the valency and frequency of the elements in the composition of formula I other than oxygen,
wherein
    a ratio of Co/Fe is from 2 to 3.5,
    a ratio of Co/Mo is from 0.55 to 0.7,
    the catalyst is annular in shape, and
    the catalyst is unsupported.

2. The catalyst according to claim 1, wherein the stoichiometric coefficient a ranges from 1.5 to 2.5.

3. The catalyst according to claim 2, wherein the stoichiometric coefficient a ranges from 2.0 to 2.5.

4. The catalyst according to claim 1, wherein the stoichiometric coefficient b ranges from 5 to 8.

5. The catalyst according to claim 4, wherein the stoichiometric coefficient b ranges from 6 to 8.

6. The catalyst according to claim 1, wherein the stoichiometric coefficient c ranges from 2 to 4.

7. The catalyst according to claim 6, wherein the stoichiometric coefficient c ranges from 2.5 to 3.5.

8. The catalyst according to claim 1, wherein the molar Co/Fe ratio ranges from 2 to 3.3.

9. The catalyst according to claim 8, wherein the molar Co/Fe ratio ranges from 2 to 3.

10. The catalyst according to claim 1, wherein the annular shape comprises an annular geometry wherein a length is from 2 to 11 mm, an external diameter is from 2 to 11 mm and a wall thickness is from 0.5 to 5 mm.

11. The catalyst according to claim 1, wherein the annular shape comprises an annular geometry wherein a length is from 2.8 to 3.2 mm, an external diameter is from 5.5 to 7 mm and an internal diameter is from 3.5 to 5 mm.

12. The catalyst according to claim 1, wherein the annular shape comprises rings whose external diameter ranges from 2 to 10 mm, whose internal ring diameter is at least 1 mm, whose wall thickness ranges from 0.5 to 2 mm and whose length ranges from 2 to 10 mm.

13. The catalyst according to claim 1, wherein a specific surface area of the catalyst is from 5 to 20 $m^2/g$ and a total pore volume of the catalyst is from 0.1 to 1 $cm^3/g$.

14. The catalyst according to claim 13, wherein the specific surface area is from 5 to 15 $m^2/g$ and the total pore volume is 0.1 to 0.8 $cm^3/g$.

* * * * *